US010583255B2

(12) United States Patent
Maxfield

(10) Patent No.: US 10,583,255 B2
(45) Date of Patent: Mar. 10, 2020

(54) MEDICAMENT CONTAINER ASSEMBLY FOR A MEDICAMENT DELIVERY DEVICE

(71) Applicant: SHL Medical AG, Zug (CH)

(72) Inventor: Brian Maxfield, Boca Raton, FL (US)

(73) Assignee: SHL Medical AG, Zug (CH)

(*) Notice: Subject to any disclaimer, the term of this patent is extended or adjusted under 35 U.S.C. 154(b) by 209 days.

(21) Appl. No.: 15/220,552

(22) Filed: Jul. 27, 2016

(65) Prior Publication Data
US 2018/0028756 A1 Feb. 1, 2018

(51) Int. Cl.
A61M 5/31 (2006.01)
A61M 5/24 (2006.01)
(Continued)

(52) U.S. Cl.
CPC ............ *A61M 5/3134* (2013.01); *A61M 5/20* (2013.01); *A61M 5/24* (2013.01); *A61M 5/3202* (2013.01); *A61M 5/3204* (2013.01); A61M 2005/2407 (2013.01); A61M 2005/2437 (2013.01); A61M 2207/00 (2013.01)

(58) Field of Classification Search
CPC .... A61M 5/24; A61M 5/3134; A61M 5/3202; A61M 5/3204; A61M 2005/2403; A61M 2005/2407; A61M 2005/2433; A61M 2005/2437; A61M 2005/244; A61M 2005/2485; A61M 2005/2492; A61J 1/1412
See application file for complete search history.

(56) References Cited

U.S. PATENT DOCUMENTS 5,002,537 A * 3/1991 Hoffman ................. A61M 5/24 604/232
8,715,246 B2 5/2014 Giambattista et al.
(Continued)

FOREIGN PATENT DOCUMENTS

CN 102470217 A 5/2012
CN 105246528 A 1/2016
WO 2013156346 A2 10/2013

OTHER PUBLICATIONS

International Search Report Issued in International Application No. PCT/EP2017/076107 dated Oct. 24, 2017.
(Continued)

Primary Examiner — Nathan R Price
Assistant Examiner — Dung T Ulsh
(74) Attorney, Agent, or Firm — McDonnell Boehnen Hulbert & Berghoff LLP

(57) ABSTRACT

The present disclosure relates to a medicament container assembly (11) for a medicament delivery device, comprising: an elongated body (3) configured to receive a medicament container (17) and provided with a radially flexible first gripper arm (3f) extending in the axial direction of the body (3) and an oppositely arranged radially flexible second gripper arm (3g) extending in the axial direction of the body (3), wherein the first gripper arm (3g) and the second gripper arm (3f) are configured to support a neck portion of a medicament container, and a clamp member (13) configured to be arranged radially outside of the first gripper arm (3f) and the second gripper arm (3g), to press the first gripper arm (3f) and the second gripper arm (3g) radially inwards, to prevent proximal displacement of a medicament container.

24 Claims, 8 Drawing Sheets

(51) Int. Cl.
*A61M 5/32* (2006.01)
*A61M 5/20* (2006.01)

(56) References Cited

U.S. PATENT DOCUMENTS

| | | | |
|---|---|---|---|
| 2012/0143143 A1 | 6/2012 | Giambattista et al. | |
| 2014/0243753 A1* | 8/2014 | Bostrom | A61M 5/3202 |
| | | | 604/198 |
| 2014/0257192 A1* | 9/2014 | Morgan | A61M 5/3137 |
| | | | 604/189 |
| 2016/0008542 A1 | 1/2016 | Hirschel et al. | |
| 2016/0243315 A1* | 8/2016 | Perche | A61M 5/3204 |
| 2017/0014578 A1* | 1/2017 | Bunch | A61M 5/3202 |
| 2018/0133407 A1* | 5/2018 | Kemp | A61M 5/2033 |

OTHER PUBLICATIONS

Search Report issued in Chinese Patent Application No. 106123510 dated Aug. 27, 2018.

* cited by examiner

US 10,583,255 B2

MEDICAMENT CONTAINER ASSEMBLY FOR A MEDICAMENT DELIVERY DEVICE

TECHNICAL FIELD

The present disclosure generally relates to medical devices. In particular, it relates to a medicament container assembly for a medicament delivery device, to a sub-assembly comprising a medicament container assembly, a medicament delivery device comprising a medicament container assembly, and to a method of assembling a sub-assembly for a medicament delivery device.

BACKGROUND

A medicament delivery device may have a housing or body configured to receive a medicament container. For this purpose, the medicament delivery device may have a medicament container holder which holds the medicament container in place inside the housing.

WO 2013/156346 A2 discloses a medicament delivery device including a medicament container comprising a movable plunger, a neck portion and a delivery member unit. The medicament delivery device also has a housing having a proximal open end and an opposing distal open end and a drive unit arranged at the distal end of the housing and configured to apply a force on the movable plunger, and a C-shaped tubular body comprising a longitudinally extending slit/gap such that the C-shaped tubular body can be attached to the neck portion of the medicament container forming a container unit. The C-shaped tubular body further comprises inner support means configured to interact with the neck portion and with the delivery member unit of the medicament container such that the medicament container is prevented from being moved in relation to the C-shaped tubular body, after the medicament container is attached to the C-shaped tubular body, and outer support means configured to interact with corresponding support means of the housing such that the C-shaped tubular body is prevented from being moved in relation to the housing after the container unit is arranged within the housing through the distal open end.

SUMMARY

The C-shaped tubular body disclosed in WO 2013/156346 A2 can expand over the neck portion of the medicament container when pushed in the proximal direction during assembly, so that it moves distally from the neck portion and onto the main body of the medicament container. This could potentially change the position of the medicament container inside the housing, and thus of the delivery member, which could result in medicament expulsion at an incorrect penetration depth.

In view of the above, a general object of the present disclosure is to provide a medicament container assembly for a medicament delivery device which solves or at least mitigates the problems of the prior art.

There is hence according to a first aspect of the present disclosure provided a medicament container assembly for a medicament delivery device, comprising: an elongated body configured to receive a medicament container and provided with a radially flexible first gripper arm extending in the axial direction of the body and an oppositely arranged radially flexible second gripper arm extending in the axial direction of the body, wherein the first gripper arm and the second gripper arm are configured to support a neck portion of a medicament container, and a clamp member configured to be arranged radially outside of the first gripper arm and the second gripper arm, to press the first gripper arm and the second gripper arm radially inwards, to prevent proximal displacement of a medicament container.

The clamp member is configured to provide radial pressure onto the first gripper arm and the second gripper arm, thereby maintaining their radial position when the clamp member is mounted around them. The first gripper arm and the second gripper arm are hence not able to expand radially outwards, in case there is provided pressure in the proximal direction onto the medicament container. The medicament container will therefore not be able to move in the proximal direction when the medicament container has been installed correctly in the medicament container assembly.

According to one embodiment the body has a support structure extending between and provided on opposite inner surfaces of the body, wherein the support structure has a central tubular portion provided with an axially extending through-opening for receiving a medicament container, and wherein the first gripper arm and the second gripper arm form part of the tubular portion.

According to one embodiment the clamp member has a through-opening configured to receive the central tubular portion.

According to one embodiment the first gripper arm has a gripper portion provided at a distal end thereof.

According to one embodiment the second gripper arm has a gripper portion provided at a distal end thereof.

According to one embodiment the clamp member is tubular.

According to one embodiment the clamp member has a proximal end flange extending radially inwards and configured to bear against a proximal end face of the first gripper arm and a proximal end face of the second gripper arm.

There is according to a second aspect of the present disclosure provided a sub-assembly for a medicament delivery device, comprising: a medicament container assembly according to the first aspect, and a cap assembly for a medicament delivery device, comprising: a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses, and an elongated squeeze member configured to be received in the distal opening of the tubular body, and having a longitudinally extending channel configured to receive a delivery member shield, and which squeeze member has radial arms flexible in the radial direction and forming part of a wall of the channel, wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap, wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel, wherein the cap assembly is configured to be assembled with the body of the medicament container assembly.

According to one embodiment the cam structure is annular in a radial plane and comprises a plurality of elevated portions with a cut-out having oppositely inclined surfaces provided between each adjacent pair of elevated portions, in the circumferential direction of the cam structure.

According to one embodiment the proximal end face of the squeeze member comprises a plurality of elevated portion with a cut-out having oppositely inclined surfaces provided between each adjacent pair of elevated portions of the proximal end face, in the circumferential direction of the squeeze member.

According to one embodiment each elevated portion of the squeeze member is configured to bear against a region of a cut-out of the cam structure closer to an elevated portion of the cam structure than to a lowest elevational point of the cut-out, in the first position of the squeeze member.

According to one embodiment the elevated portions of the squeeze member are configured to engage with the cut-outs of the cam structure in the second position of the squeeze member.

According to one embodiment at least two of the radial arms are arranged opposite to each other in a radial plane of the squeeze member, causing the two radial arms to move towards each other in the second position of the squeeze member.

According to one embodiment two of the radial arms are arranged in a first radial plane of the squeeze member, and wherein two other radial arms are arranged in a second radial plane axially spaced apart from the first radial plane.

According to one embodiment the two radial arms arranged in the first plane are arranged 90 degrees offset in the circumferential direction relative to the two arms arranged in the second plane.

According to one embodiment the radial recesses have inclined surfaces in the circumferential direction allowing the radial arms to disengage when the squeeze member is rotated while displaced from the first position to the second position.

According to one embodiment the radial arms have an increasing thickness in a direction from their point of attachment towards their end portions, wherein the thickness of each end portion is thicker than a wall thickness of the channel.

According to one embodiment the radial recesses extend in the longitudinal direction along a majority of the length of the inner walls of the tubular body.

There is according to a third aspect of the present disclosure provided a medicament delivery device comprising: a medicament container assembly according to the first aspect.

One embodiment comprises a housing, wherein the body of the medicament container assembly is the housing.

One embodiment comprises a cap assembly comprising: a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses, and an elongated squeeze member configured to be received in the distal opening of the tubular body, and having a longitudinally extending channel configured to receive a delivery member shield, and which squeeze member has radial arms flexible in the radial direction and forming part of a wall of the channel, wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap, wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel, wherein the cap assembly is configured to be assembled with the body of the medicament container assembly.

One embodiment comprises a medicament container provided with a delivery member and configured to be arranged in the body, and a delivery member shield configured to shield the delivery member, wherein the delivery member shield is configured to be received by the squeeze member.

There is according to a fourth aspect of the present disclosure provided a method of assembling a sub-assembly for a medicament delivery device, comprising: A) providing a medicament container assembly according to the first aspect, B) inserting a medicament container including a delivery member shield in the body from a distal end opening of the body and moving the medicament container in the proximal direction until a neck portion of the medicament container moves past the distal ends of the first gripper arm and the second gripper arm, and the delivery member shield extends through a proximal opening of the body, C) moving the clamp member over the delivery member shield and inserting the clamp member into the body through the proximal opening of the body, and D) moving the clamp member in the distal direction over the first gripper arm and the second gripper arm, and pushing the medicament container distally until the clamp member reaches an end position and the first gripper arm and the second gripper arm snaps around the neck portion of the medicament container.

One embodiment comprises: a) providing a cap assembly comprising: a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses, and an elongated squeeze member configured to be received in the distal opening of the tubular body, and having a longitudinally extending channel configured to receive a delivery member shield, and which squeeze member has radial arms flexible in the radial direction and forming part of a wall of the channel, wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap, wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel, b) inserting the squeeze member into the distal opening of the cap and moving the squeeze member towards the bottom structure until the proximal end face of the squeeze member contacts the bottom structure to obtain the first position of the squeeze member, and c) assembling the cap with the squeeze member arranged therein with the medicament container assembly such that the squeeze member receives the delivery member shield.

According to one embodiment step c) includes moving a distal end face of the squeeze member towards a proximal surface of the clamp member, causing the squeeze member to move proximally inside the cap from the first position to the second position and the radial arms to squeeze the delivery member shield.

According to one embodiment the delivery member shield is a rigid needle shield.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
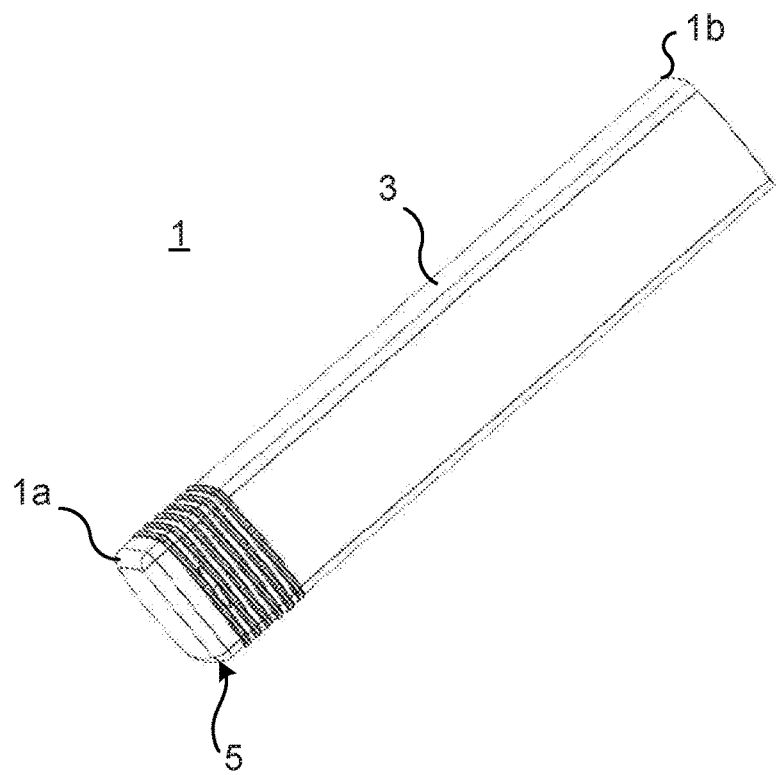
FIG. 1 is a perspective view of an example of a medicament delivery device without an activation assembly.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which is farthest from the proximal end of the medicament delivery device, when the cap assembly is properly mounted onto a medicament delivery device. The proximal end of a medicament delivery device is that end which is to be pointed towards the injection site during medicament injection. The same considerations also apply when referring to any component of the cap assembly. The "distal end" is the opposite end relative to the proximal end. With "proximal direction" and, equivalently, "proximally" is meant a direction from the distal end towards the proximal end, along the central axis of the safety mechanism.

With "distal direction" or "distally" is meant the opposite direction to "proximal direction". The same definition also applies for the medicament container and any component thereof.

The cap assembly disclosed herein includes a cap and an elongated squeeze member. The cap is configured to be mounted to a proximal end of a medicament delivery device, for example to the housing, or body, of a medicament delivery device. The cap has a tubular body which has a distal opening extending along the central axis of the tubular body.

The tubular body has a bottom structure which defines the proximal end wall of the distal opening. The bottom structure has a cam structure, provided inside the tubular body, in particular inside the distal opening. The tubular body has inner walls, i.e. the inner walls of the distal opening provided with radial recesses.

The squeeze member is configured to be received by the tubular body, in particular in the distal opening. The squeeze member has a longitudinally extending channel configured to receive a delivery member shield. The squeeze member furthermore has radial arms that are flexible in the radial direction. The radial arms form part of a channel wall(s). The squeeze member furthermore has a proximal end face configured to cooperate with the cam structure of the cap. The squeeze member is configured to be axially displaceable from a first position in which the proximal end face bears against the cam structure to a second position in which the squeeze member is received further by the cap. This axial displacement causes rotation of the squeeze member relative to the cap, and is obtained due to the cooperating proximal end face of the squeeze member and the cam structure of the cap.

The radial arms extend radially outside the outer surface of the squeeze member when the squeeze member is arranged in the first position. In the first position, each radial arm is received by a respective radial recess of the tubular body. When the squeeze member is rotated, the radial arms disengage from the radial recesses, and as the squeeze member rotates so that the radial arms are moved in the circumferential direction away from their respective radial recess, the radial arms are pressed radially inwards by the inner walls of the tubular body. This causes the radial arms to extend radially inwards of the inner surface of the channel of the squeeze member, reducing a cross-sectional area of the channel. The radial arms may thereby provide radial pressure onto a delivery member shield received by the squeeze member. The cap assembly can thus engage with the delivery member shield such that when the cap assembly is removed from a medicament delivery device, the delivery member shield is removed simultaneously.

With reference to FIGS. 1-10 an example of a cap assembly will be described.

FIG. 1 shows a perspective view of a medicament delivery device 1, which in the present case may also be seen as a sub-assembly of a medicament delivery device, because the depicted example does not comprise an activation assembly, which is to be mounted to a distal end of the medicament delivery device 1.

The exemplified medicament delivery device 1 shown in FIG. 1 has a proximal end 1a and a distal end 1b, and comprises a body, or housing, 3, and a cap assembly 5.

Figure 2:
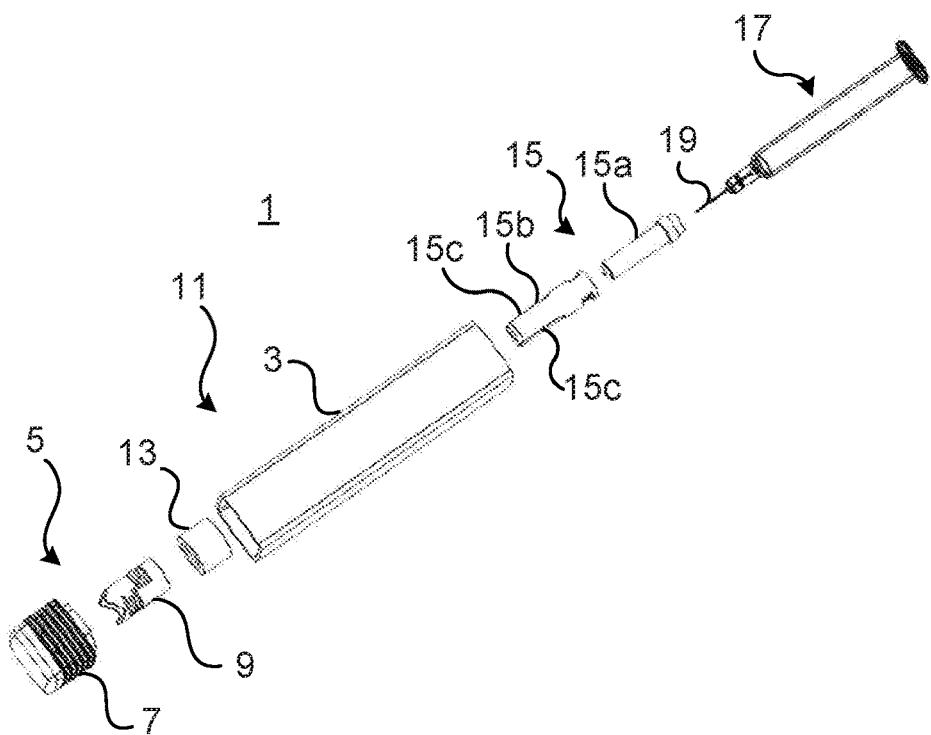
FIG. 2 shows an exploded view of the medicament delivery device in FIG. 1.

Turning now to FIG. 2, an exploded view of the medicament delivery device 1 is shown. The medicament delivery device 1 comprises the cap assembly 5, which comprises a cap 7 and a squeeze member 9, a medicament container assembly 11, which comprises the body 3 and a clamp member 13. The medicament delivery device 1 may further include a delivery member shield 15 and a medicament container 17 including a delivery member 19.

According to the example shown in FIG. 2, the medicament container 17 is a syringe and the delivery member 19 is a needle. Moreover, the exemplified the delivery member shield 15 includes a flexible inner member 15a configured to receive the delivery member 19 and a rigid outer member 15b configured to receive the flexible inner member 15a. The rigid outer member 15b has chamfered outer surfaces 15c extending parallel with each other in the longitudinal direction of the delivery member shield 15. The exemplified delivery member shield 15 is a rigid needle shield, but could alternatively be a flexible needle shield.

Figure 3:
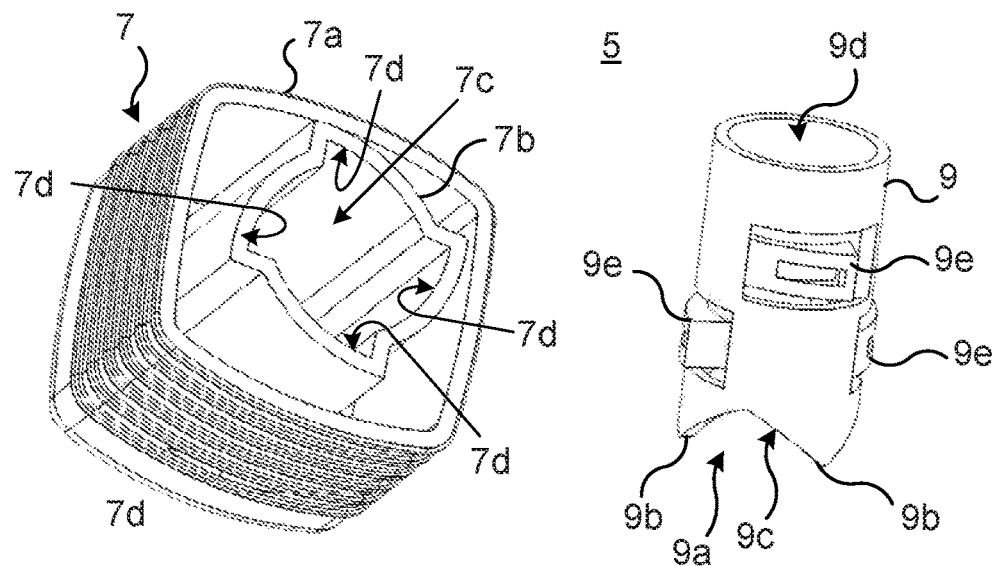
FIG. 3 shows an example of a cap assembly.

FIG. 3 shows a detailed view of the cap assembly 5. The exemplified cap 7 has an outer body 7a and an inner tubular body 7b, coaxially arranged with the outer body. The tubular body 7b has an axially extending distal opening 7c.

The tubular body 7b is configured to receive the squeeze member 9 in the distal opening 7c.

The tubular body 7b has a plurality of radial recesses 7d. The radial recesses 7d extend in the longitudinal direction along a majority of the axial length of the tubular body 7b, and thus of the distal opening 7c.

The squeeze member 9 is elongated and has a tubular shape. The squeeze member 9 has a channel 9d extending in the longitudinal direction through the squeeze member 9, configured to receive the delivery member shield 15.

The squeeze member 9 furthermore has a proximal end face 9a comprising a plurality of elevated portions 9b. Between each pair of adjacent pair of elevated portions 9b is a cut-out 9c with oppositely inclined or sloping surfaces. The proximal end face 9a is hence provided with a plurality of teeth in the circumferential direction of the squeeze member 9, with a gradually increasing and decreasing elevation.

The squeeze member 9 comprises a plurality of radial arms 9d which are flexible in the radial direction. The radial arms 9d extend the circumferential direction from the main body of the squeeze member 9 and have an increasing thickness towards their end portions relative to the point of attachment to the main body of the squeeze member 9. Hereto, the end thickness of each radial arm is substantially thicker than the thickness of the channel wall.

The radial arms 9e form part of the channel wall. The radial arms 9e are by default configured to flex radially outwards from the outer surface of the squeeze member 9, as shown in FIG. 3. Hereto, the radial arms 9e protrude radially from the outer surface of the main body of the squeeze member 9 when no external force is applied to the radial arms 9e. The radial arms 9e are configured to slide axially in a respective radial recess 7d of the cap 7, when the squeeze member 9 is moved linearly in the distal opening 7c of the tubular body 7b. The radial recess 7d have inclined surfaces in the circumferential direction, allowing the radial arms 9e to disengage from the radial recesses 7d when the squeeze member 9 is rotated while being displaced in the distal opening 7c, from a first position to a second position. The radial recesses 7d and the radial arms 9e may be seen to form a ratchet configuration, with the radial arms 9e being flexible radially inwards when the squeeze member 9 disengage from the radial recesses 7d and the squeeze member 9 is being rotated.

According to the example shown in FIG. 3, the squeeze member 9 has a plurality of arms 9e in a first radial plane along the axial direction of the squeeze member 9, and a plurality of radial arms 9e in a second plane axially spaced apart from the first plane. The exemplified squeeze member 9 hence has several layers of radial arms 9e, in the axial direction of the squeeze member 9.

Figure 4:
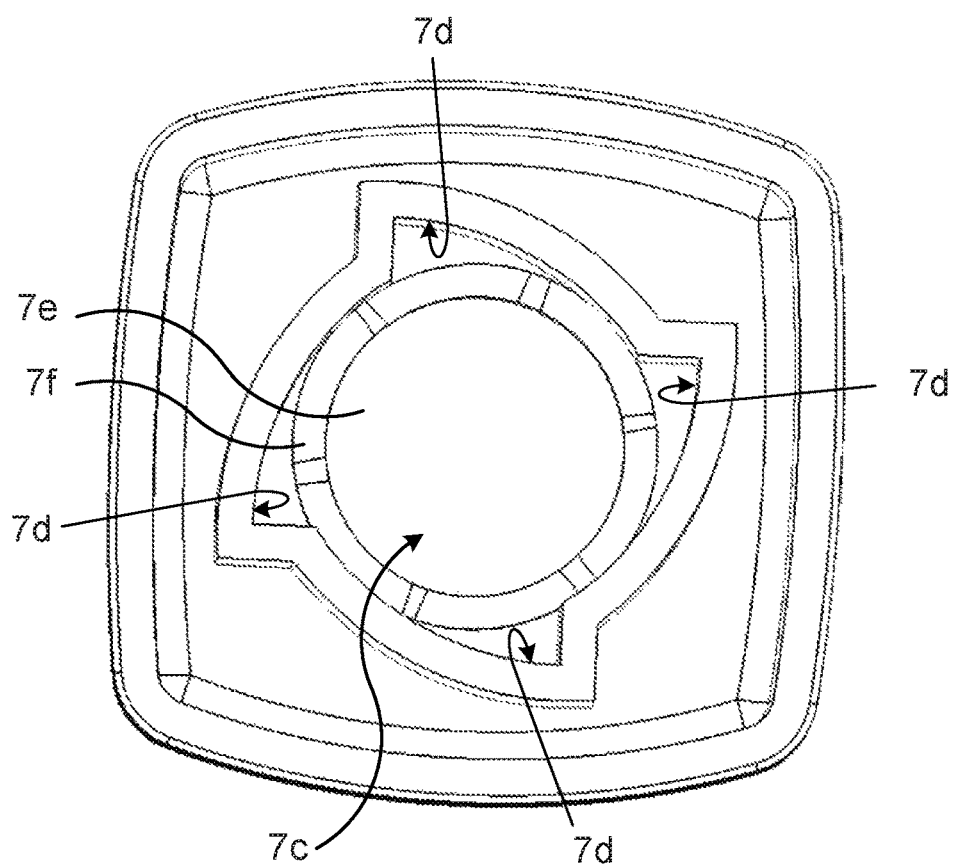
FIG. 4 is a top view of a cap.

FIG. 4 shows a top view of the cap 7, in particular seen from the distal end of the cap 7. The cap 7 has a bottom structure 7e, which defines a distal end wall or surface of the distal opening 7c. The bottom structure 7e has a cam structure 7f, which according to the present example is annular in a radial plane. The cam structure 7f is configured to cooperate with the proximal end face 9a of the squeeze member 9.

Figure 5:
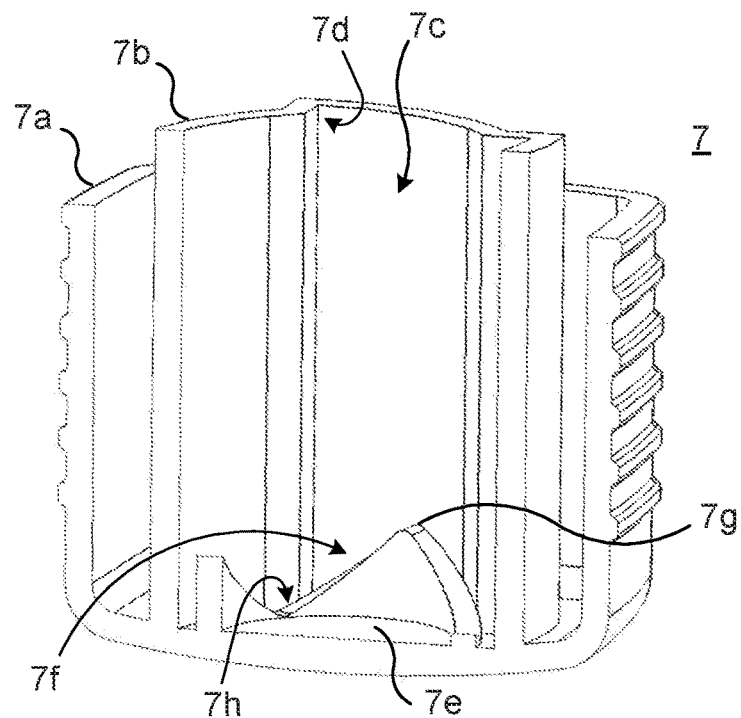
FIG. 5 is a longitudinal section of the cap in FIG. 4.

FIG. 5 shows a longitudinal section of the cap 7. The cam structure 7f has a plurality of slanting surfaces, forming a gradually increasing and decreasing teeth-like structure in the circumferential direction. Hereto, the cam structure 7f has a plurality of elevated portions 7g, of which one can be seen in FIG. 5, and cut-outs 7h with oppositely arranged inclined surfaces. Between each pair of adjacent elevated portion 7g, there is provided a cut-out 7h. This configuration of the cam structure 7f allows for cooperation with the corresponding structure of the proximal end face 9a of the squeeze member 9, as will be described in more detail in the following.

Figure 6:
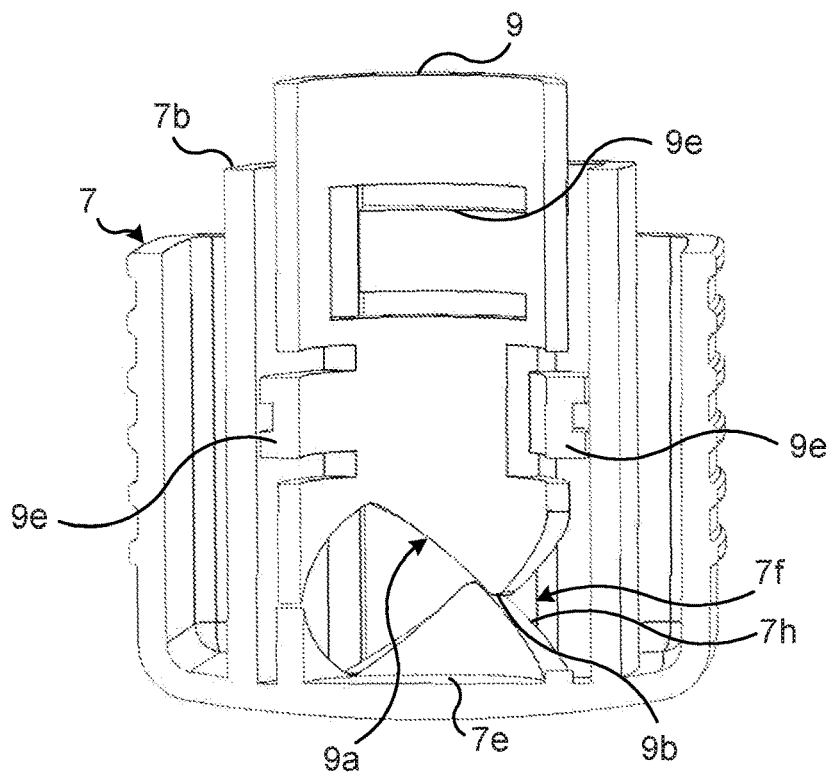
FIG. 6 shows the squeeze member arranged in the cap in a first position of the squeeze member.

FIG. 6 shows the squeeze member 9 arranged inside the tubular body 7b of the cap 7. The squeeze member 9 is arranged in a first position relative to the cap 7. Here, the proximal end face 9a of the squeeze member 9 bears against the cam structure 7f arranged inside the tubular body 7b. Each elevated portion 9b of the squeeze member 9 bears against a respective top portion of the cut-out 7h, closer to an elevated portion of the cam structure 7f than to the lowest elevational point of the cut-out 7h.

Figure 7:
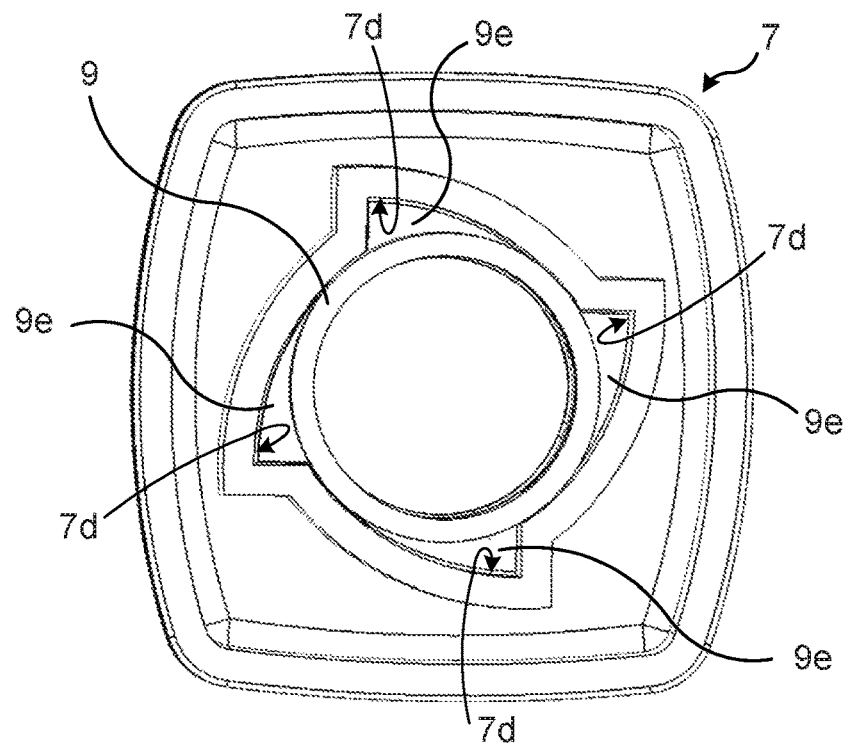
FIG. 7 is a top view of the cap assembly shown in FIG. 6.

As shown in the top view of FIG. 7, each radial arm 9e of the squeeze member 9 is arranged in a respective radial recess 7d of the inner walls of the tubular body 7b when the squeeze member 9 is in the first position.

Figure 8:
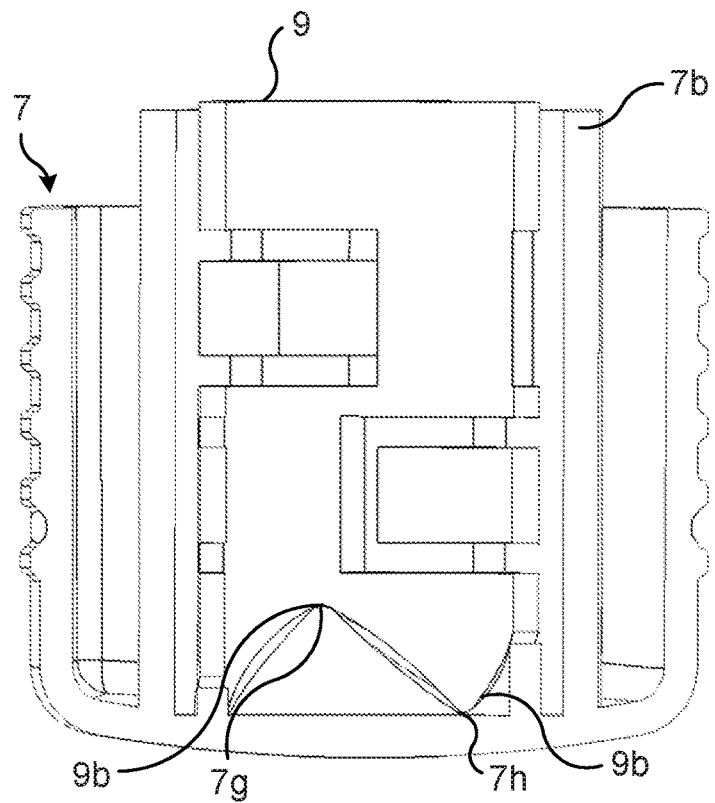
FIG. 8 is a longitudinal section of the squeeze member arranged in the cap in a second position of the squeeze member.

FIG. 8 shows the squeeze member 9 in a second position. In the second position, the squeeze member 9 has been axially displaced relative to the first position shown in FIG. 6. In particular, the squeeze member 9 has been further received by the tubular body 7b. Due to this proximal displacement of the squeeze member 9 the proximal end face 9a and the cam structure 7f have cooperated, causing the squeeze member 9 to rotate relative to the cap 7. Hereto, the elevated portions 9b of the proximal end face 9a have slid down to the lowest elevational points of the cut-outs 7h of the cam structure 7f. Moreover, the elevated portions 7g of the cam structure 7f have been fully received by the cut-out 9c of the proximal end face 9a of the squeeze member 9.

Figure 9:
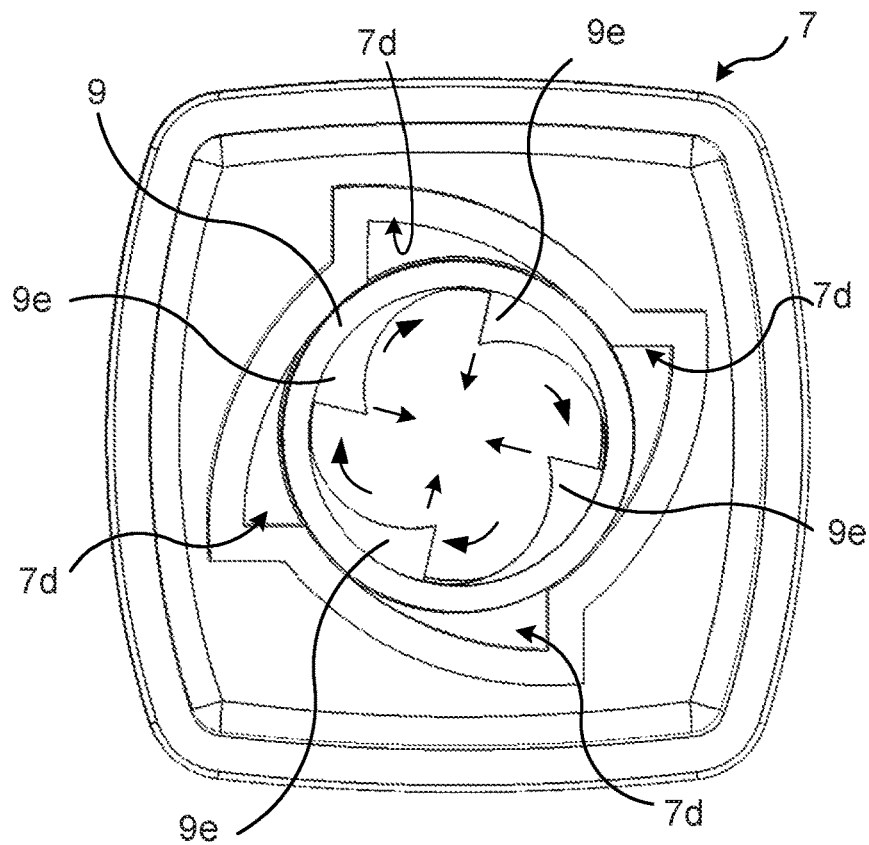
FIG. 9 is a top view of the cap assembly shown in FIG. 8.

In FIG. 9, a top view of the situation shown in FIG. 8 is depicted. The radial arms 9e have disengaged from the radial recesses 7d as the squeeze member 9 is moved proximally from the first position to the second position, causing the squeeze member 9 to rotate, as indicated by the arrows showing rotation. This causes the radial arms 9e to bear against the inner walls of the tubular body 7b, outside the radial recesses 7d, which are radially closer to the central axis of the tubular body 7b. The radial arms 9e are therefore pressed or flexed radially inwards. The radial arms 9e have end portions that are thicker than the wall thickness of the channel 9d, and therefore, the radial arms 9e are pressed into the channel 9d, reducing the cross-sectional area of the channel 9d. When the delivery member shield 15 is arranged in the channel 9d, the radial arms 9e will engage with, or press against, the outer surface of the delivery member shield 9d.

Figure 10:
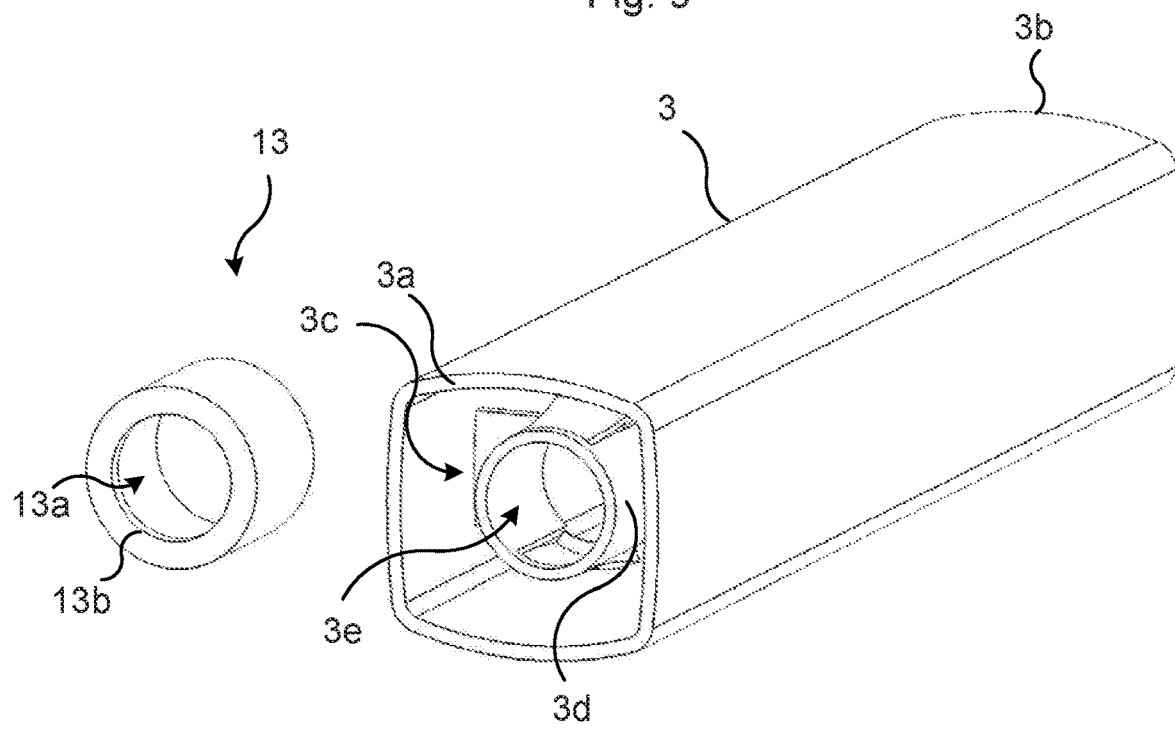
FIG. 10 shows a perspective view of an example of a medicament container assembly.

FIG. 10 shows the medicament container assembly 11. It should be noted that other medicament container assemblies than the one described herebelow may be used in conjunction with the cap assembly 5 previously described. Similarly, the below described medicament container assembly 11 may be used in conjunction with other cap assemblies than the exemplified cap assembly 5.

The exemplified medicament container assembly 11 includes the body 3 and the clamp member 13.

The clamp member 13 is tubular and has a through-opening 13a extending in the longitudinal direction of the clamp member 13. The clamp member 13 furthermore has a proximal end flange 13, or support surface, extending radially inwards.

The body 3 has an elongated shape and is configured to receive the medicament container 17. The body 3 has a proximal end 3a and a distal end 3b and a support structure 3c arranged inside the body 3, closer to the proximal end 3a than to the distal end 3b. The support structure 3c extends between opposite inner surfaces of the body 3. The support structure 3c is provided on, or attached to, the opposite inner surfaces of the body 3. The support structure 3c has a central tubular portion 3d provided with an axially extending through-opening 3e configured to receive the medicament container 17.

Figure 11:
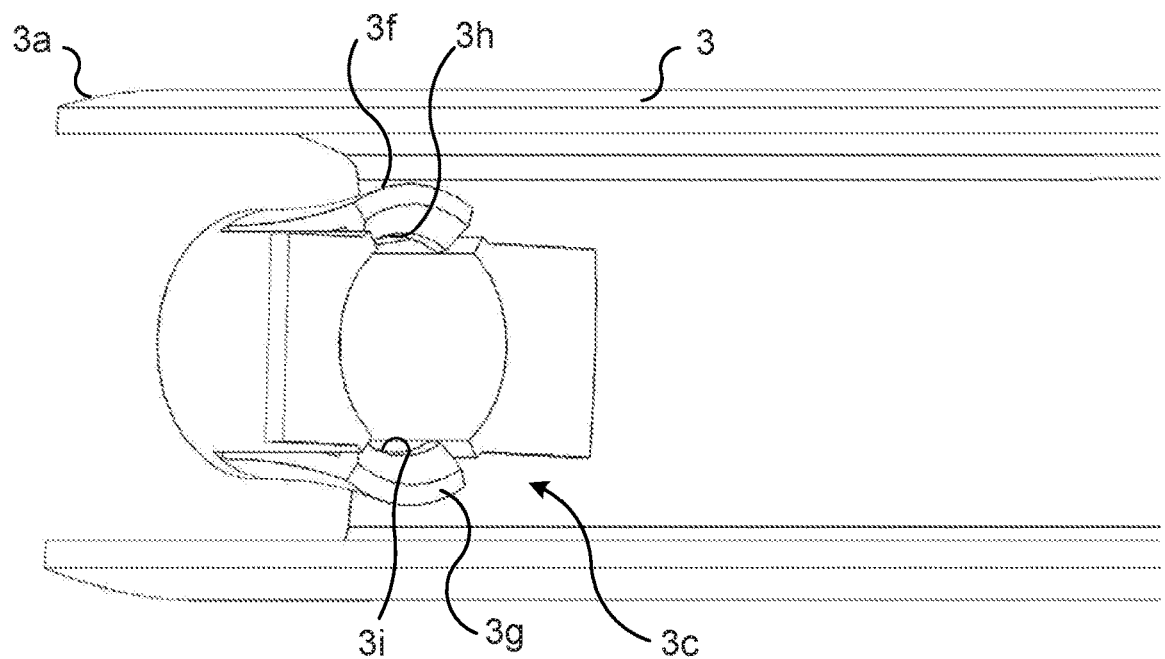
FIG. 11 shows a longitudinal section of a proximal portion of an elongated body of the medicament container assembly.

As shown in FIG. 11, the body 3 furthermore has a radially flexible first gripper arm 3f and a radially flexible second gripper arm 3g arranged opposite relative to the first gripper arm 3f. The first gripper arm 3f and the second gripper arm 3g extend in the axial direction of the body 3.

The first gripper arm 3f and the second gripper arm 3g are configured to support a neck portion of the medicament container 17. According to the example shown in FIG. 11, the first gripper arm 3f and the second gripper arm 3g form part of the tubular portion 3d.

The first gripper arm 3f has a gripper portion 3h provided at a distal end of the first gripper arm 3f, extending radially inwards. The second gripper arm 3g has a gripper portion 3i provided at a distal end of the second gripper arm 3g, extending radially inwards.

The clamp member 13 is configured to receive the tubular portion 3d of the body 3. In particular, the clamp member 13 is configured to be brought around the tubular portion 3d from the proximal end 3a of the body 3, and moved around the tubular portion 3d such that the first gripper arm 3f and the second gripper arm 3g are received by the clamp member 13 and pressed radially inwards by the inner surface of the clamp member 13. When the clamp member 13 has been set in its end position during assembly, the proximal end flange 13b of the clamp member 13 bears against the proximal end of the tubular portion 3d.

With reference to FIGS. 12-15 methods of assembling a sub-assembly will now be described.

Figure 12:
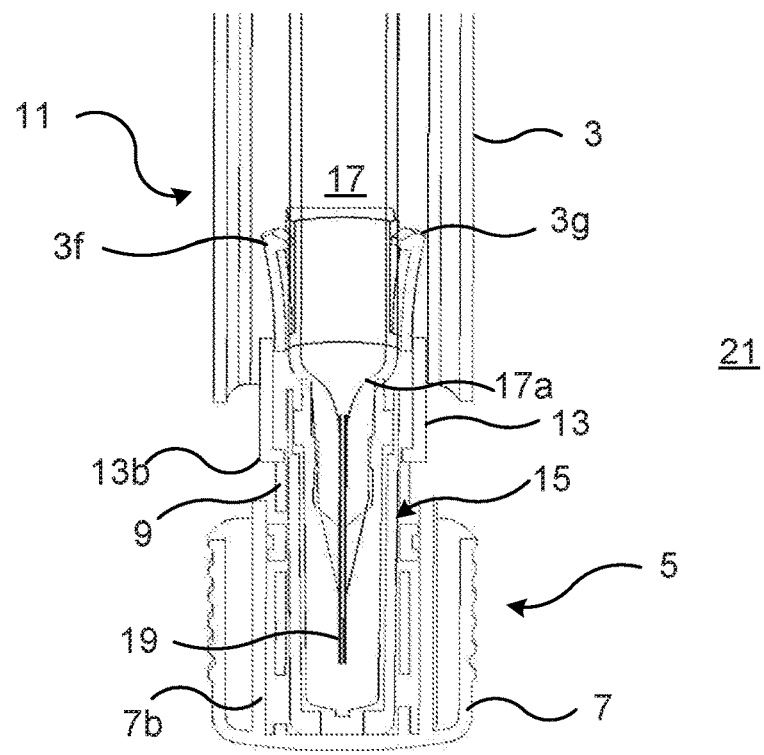
FIG. 12 shows a longitudinal section of a sub-assembly comprising the cap assembly and the medicament container assembly during assembly.

FIG. 12 shows a longitudinal section of an example of a sub-assembly. Sub-assembly 21 includes the cap assembly 5 and the medicament container assembly 11. FIG. 12 shows the sub-assembly 21 during assembly. The squeeze member 9 is in the first position inside the tubular body 7b of the cap 7, and the delivery member shield 15 is arranged in the channel of the squeeze member 9. The medicament container 17 has been arranged inside the body 3, and extends through the through-opening 3e of the tubular portion 3d, with a neck portion 17a of the medicament container 17 extending proximally beyond the tubular portion 3d. The delivery member 19 is arranged in the delivery member shield 15.

Figure 13:
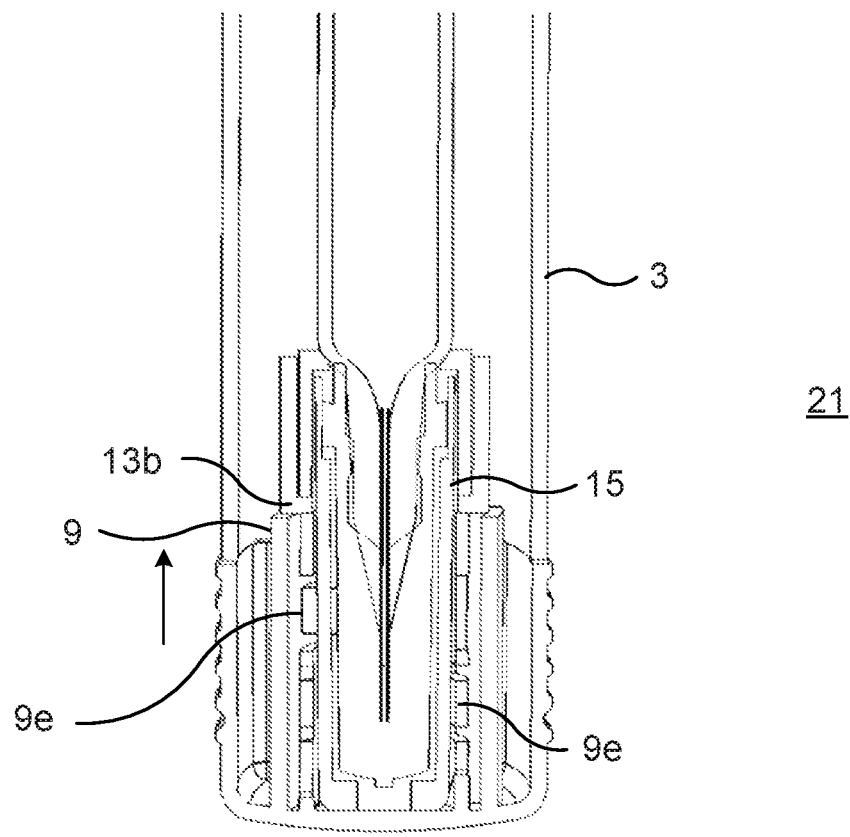
FIG. 13 shows a longitudinal section of the sub-assembly in FIG. 12 when the cap assembly and the medicament container assembly have been assembled.

In FIG. 13, the sub-assembly 21 is shown in an assembled state. The distal end face of the squeeze member 9 was pushed towards the proximal end flange 13b of the clamp member 13 as the cap assembly 5 and the medicament container assembly 11 were moved towards each other, causing the squeeze member 9 to move from the first position to the second position, and thereby rotate due to the cooperation between the cam structure 7f of the cap 7 and the proximal end face 9a of the squeeze member 9. The radial arms 9e of the squeeze member 9 have thus moved radially inwards as they were pressed towards the inner walls of the tubular body 7b, outside the radial recesses 7d, causing the radial arms 9e to engage with the delivery member shield 15.

Figure 14:
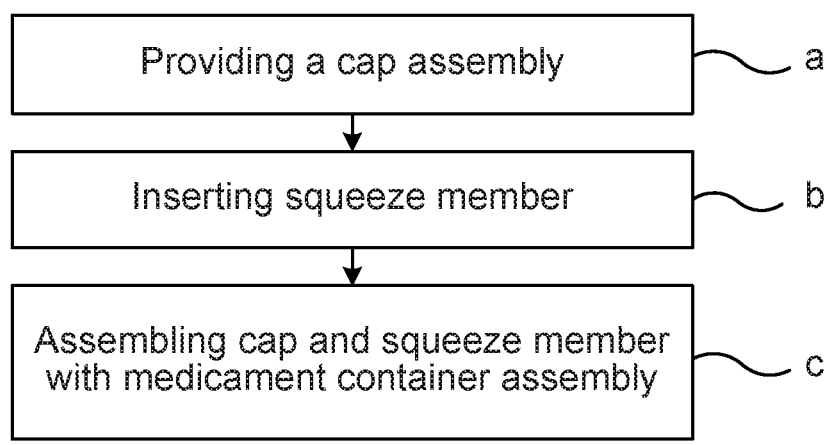
FIG. 14 is a flowchart showing a method of assembling a sub-assembly including the cap assembly and the medicament container assembly.

FIG. 14 shows a flowchart of a method of assembling a sub-assembly, for example sub-assembly 21.

In a step a) the cap assembly 5 is provided.

In a step b), the squeeze member 9 is inserted into the distal opening 7c of the tubular body 7b of the cap 7. The squeeze member 9 is moved towards the bottom structure 7e of the tubular body 7b until the proximal end face 9a of the squeeze member 9 contacts the bottom structure 7e, with each elevated portion 9b of the squeeze member 9 being arranged closer to an elevated portion 7g of the cam structure 7f than to the lowest elevational point of the corresponding cut-outs 7h of the cap 7. The squeeze member 9 is thus set in the first position.

In a step c) the cap 7 with the squeeze member 9 arranged therein is assembled with a medicament container assembly, for example medicament container assembly 11, including the medicament container 17 and the delivery member shield 15.

In examples where the cap assembly 5 is assembled with the medicament container assembly 11, the distal end of the squeeze member 9 is pushed against the proximal end flange 13b of the clamp member 13 provided around the support structure 3c of the body 3 and is moved in the distal direction, causing the squeeze member 9 to move in the proximal direction from the first position to the second position. Hence, during the assembly in step c), the squeeze member 9 is pushed further into the cap 7, moving from the first position to the second position, causing the squeeze member 9 to rotate and grip the delivery member shield 15.

It should be noted that the cap assembly 5 could alternatively be assembled with another type of medicament container assembly, provided that the medicament container assembly has a support surface against which the distal end face of the squeeze member may be pushed during assembly, to move the squeeze member from the first position to the second position.

Figure 15:
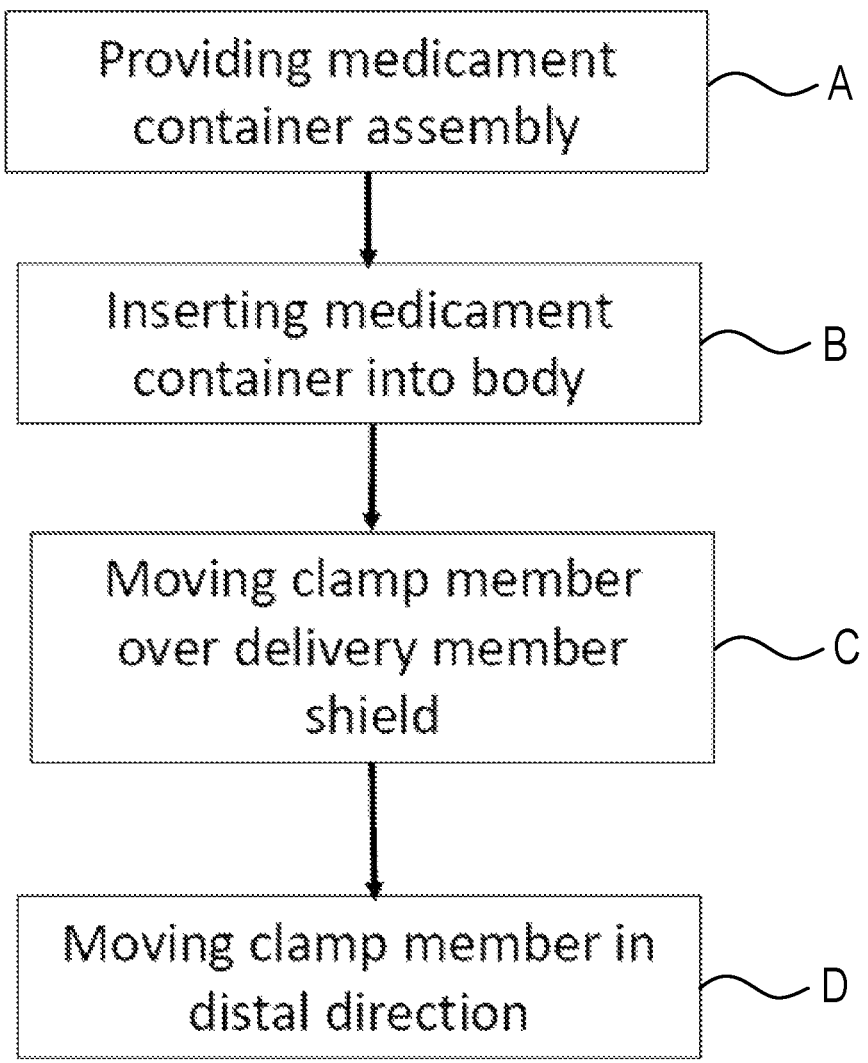
FIG. 15 is a flowchart showing a method of assembling a sub-assembly including the cap assembly and the medicament container assembly.

The medicament container assembly 11 may be assembled according to the method described by the flowchart in FIG. 15.

Hence, in a step A) the medicament container assembly 11 is provided.

In a step B) the medicament container 17 is inserted from a distal end opening of the body 3, with the delivery member 19 pointing in the proximal direction and the delivery member shield 15 being provided on the delivery member 19.

The medicament container 17 is moved in the proximal direction until the neck portion 17a of the medicament container 17 moves past the distal ends of the first gripper arm 3f and the second gripper arm 3g, and the delivery member shield 15 extends proximally through a proximal opening of the body 3.

In a step C) the clamp member 13 is moved over the delivery member shield 15, and into the body 3 through the proximal opening thereof.

In a step D) the clamp member 13 is moved in the distal direction over the tubular portion 3d, and thus over the first gripper arm 3f and the second gripper arm 3g. The first gripper arm 3f and the second gripper arm 3f are thereby bent or flexed radially inwards by the inner surface or wall of the clamp member 13.

In step D) the medicament container 17 may furthermore be pushed distally until the clamp member 13 reaches an end position, i.e. when the proximal end flange 13b bears against the proximal end of the tubular portion 3d, and the first gripper arm 3f and the second gripper arm 3g snap around the neck portion 17a of the medicament container 17, thereby providing support of the neck portion 17a.

In case that the cap assembly 5 is assembled with the exemplified medicament container assembly 11 the steps a)-c) and steps A)-D) are interconnected, in the sense that prior to step c) the medicament container assembly 11 has typically been assembled according to steps A-C, while step D) and step c) may be carried out simultaneously. Thus in step D) the clamp member 13 may be pushed distally by the squeeze member 9 and the medicament container 17 and delivery member shield 15 may be pushed distally by the cap 7, as the delivery member shield 15 is arranged in the squeeze member 9 and the cap 7 is moved distally towards the proximal end of the body 3.

The inventive concept has mainly been described above with reference to a few examples. However, as is readily appreciated by a person skilled in the art, other embodiments than the ones disclosed above are equally possible within the scope of the inventive concept, as defined by the appended claims.

I claim:

1. A medicament container assembly for a medicament delivery device, comprising:
an elongated body configured to receive a medicament container and provided with a radially flexible first gripper arm extending in the axial direction of the elongated body and an oppositely arranged radially flexible second gripper arm extending in the axial direction of the elongated body, wherein the first gripper arm and the second gripper arm are configured to support a neck portion of the medicament container, and
a clamp member configured to be moved distally over the first gripper arm and the second gripper arm into an installed position such that the first gripper arm and the second gripper arm are received through an open distal end of the clamp member, wherein in the installed position the clamp member is arranged radially outside of the first gripper arm and the second gripper arm to press the first gripper arm and the second gripper arm radially inwards to prevent proximal displacement of the medicament container,
wherein the elongated body has a support structure extending between and provided on opposite inner surfaces of the elongated body, wherein the support structure has a central tubular portion provided with an axially extending through-opening for receiving the medicament container, and wherein the first gripper arm and the second gripper arm form part of the central tubular portion,
wherein the clamp member has a proximal end flange extending radially inwards and configured to bear against a proximal end face of the first gripper arm and a proximal end face of the second gripper arm.

2. The medicament container assembly as claimed in claim 1, wherein the clamp member has a through-opening configured to receive the central tubular portion.

3. The medicament container assembly as claimed in claim 1, wherein the first gripper arm has a gripper portion provided at a distal end thereof.

4. The medicament container assembly as claimed in claim 1, wherein the second gripper arm has a gripper portion provided at a distal end thereof.

5. The medicament container assembly as claimed in claim 1, wherein the clamp member is tubular.

6. A sub-assembly for a medicament delivery device, comprising:
a medicament container assembly as claimed in claim 1, and a
cap assembly for a medicament delivery device, comprising:
a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses, and
an elongated squeeze member configured to be received in the distal opening of the tubular body, and having a longitudinally extending channel configured to receive a delivery member shield, and which squeeze member has radial arms flexible in the radial direction and forming part of a wall of the channel,
wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap,
wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel,
wherein the cap assembly is configured to be assembled with the body of the medicament container assembly.

7. The sub-assembly as claimed in claim 6, wherein the cam structure is annular in a radial plane and comprises a plurality of elevated portions with a cut-out having oppositely inclined surfaces provided between each adjacent pair of elevated portions, in the circumferential direction of the cam structure.

8. The sub-assembly as claimed in claim 6, wherein the proximal end face of the squeeze member comprises a plurality of elevated portion with a cut-out having oppositely inclined surfaces provided between each adjacent pair of elevated portions of the proximal end face, in the circumferential direction of the squeeze member.

9. The sub-assembly as claimed in claim 8, wherein each elevated portion of the squeeze member is configured to bear against a region of a cut-out of the cam structure closer to an elevated portion of the cam structure than to a lowest elevational point of the cut-out, in the first position of the squeeze member.

10. The sub-assembly as claimed in claim 8, wherein the elevated portions of the squeeze member are configured to engage with the cut-outs of the cam structure in the second position of the squeeze member.

11. The sub-assembly as claimed in claim 6, wherein at least two of the radial arms are arranged opposite to each other in a radial plane of the squeeze member, causing the two radial arms to move towards each other in the second position of the squeeze member.

12. The sub-assembly as claimed in claim 6, wherein two of the radial arms are arranged in a first radial plane of the squeeze member, and wherein two other radial arms are arranged in a second radial plane axially spaced apart from the first radial plane.

13. The sub-assembly as claimed in claim 12, wherein the two radial arms arranged in the first plane are arranged 90 degrees offset in the circumferential direction relative to the two arms arranged in the second plane.

14. The sub-assembly as claimed in claim 6, wherein the radial recesses have inclined surfaces in the circumferential direction allowing the radial arms to disengage when the squeeze member is rotated while displaced from the first position to the second position.

15. The sub-assembly as claimed in claim 6, wherein the radial arms have an increasing thickness in a direction from their point of attachment towards their end portions, wherein the thickness of each end portion is thicker than a wall thickness of the channel.

16. The sub-assembly as claimed in claim 6, wherein the radial recesses extend in the longitudinal direction along a majority of the length of the inner walls of the tubular body.

17. A medicament delivery device comprising:
a medicament container assembly as claimed in claim 1.

18. The medicament delivery device as claimed in claim 17, comprising a housing, wherein the elongated body of the medicament container assembly is the housing.

19. The medicament delivery device as claimed in claim 17, comprising a cap assembly comprising:
a cap having a tubular body defining an axially extending distal opening and configured to be mounted to a proximal end of a medicament delivery device, wherein the cap has a bottom structure defining a proximal end of the distal opening, wherein the bottom structure has a cam structure provided inside the tubular body, and wherein the tubular body has inner walls provided with radial recesses, and
an elongated squeeze member configured to be received in the distal opening of the tubular body, and having a longitudinally extending channel configured to receive a delivery member shield, and which squeeze member has radial arms flexible in the radial direction and forming part of a wall of the channel,
wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap,
wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel,
wherein the cap assembly is configured to be assembled with the body of the medicament container assembly.

20. The medicament delivery device as claimed in claim 19, comprising a medicament container provided with a delivery member and configured to be arranged in the body, and a delivery member shield configured to shield the delivery member, wherein the delivery member shield is configured to be received by the squeeze member.

21. A method of assembling a sub-assembly for a medicament delivery device, comprising:
A) providing a medicament container assembly as claimed in claim 1,
B) inserting the medicament container including a delivery member shield in the body from a distal end opening of the body and moving the medicament container in the proximal direction until a neck portion of the medicament container moves past the distal ends of the first gripper arm and the second gripper arm, and the delivery member shield extends through a proximal opening of the body,
C) moving the clamp member over the delivery member shield and inserting the clamp member into the body through the proximal opening of the body, and
D) moving the clamp member in the distal direction over the first gripper arm and the second gripper arm, and pushing the medicament container distally until the clamp member reaches an end position and the first gripper arm and the second gripper arm snaps around the neck portion of the medicament container.

22. The method as claimed in claim 21, comprising:
a) providing a cap assembly comprising:
a cap having a tubular body defining an axially extending distal opening and configured to be mounted to a proximal end of the medicament delivery device, wherein the cap has a bottom structure defining a proximal end of the distal opening, wherein the bottom structure has a cam structure provided inside the tubular body, and wherein the tubular body has inner walls provided with radial recesses, and
an elongated squeeze member configured to be received in the distal opening of the tubular body, and having a longitudinally extending channel configured to receive a delivery member shield, and which squeeze member has radial arms flexible in the radial direction and forming part of a wall of the channel, wherein the squeeze member has a proximal end face configured to cooperate with the cam structure of the cap, whereby axial displacement of the squeeze member from a first position in which the proximal end face bears against the cam structure to a second position in which the squeeze member is received further by the cap causes rotation of the squeeze member relative to the cap, wherein the radial arms are configured to engage with a respective radial recess of the tubular body in the first position of the squeeze member, and wherein the radial arms are configured to disengage from the respective radial recess when the squeeze member is displaced from the first position to the second position and rotated, whereby the flexible radial arms are pressed into the channel by the inner walls of the tubular body, reducing a cross-sectional area of the channel, b) inserting the squeeze member into the distal opening of the cap and moving the squeeze member towards the bottom structure until the proximal end face of the squeeze member contacts the bottom structure to obtain the first position of the squeeze member, and c) assembling the cap with the squeeze member arranged therein with the medicament container assembly such that the squeeze member receives the delivery member shield.

23. The method as claimed in claim 22, wherein step c) includes moving a distal end face of the squeeze member towards a proximal surface of the clamp member, causing the squeeze member to move proximally inside the cap from the first position to the second position and the radial arms to squeeze the delivery member shield.

24. The method as claimed in claim 21, wherein the delivery member shield is a rigid needle shield.

* * * * *